United States Patent [19]
Uckun et al.

[11] Patent Number: 6,124,324
[45] Date of Patent: Sep. 26, 2000

[54] THIOPHENE-ETHYL THIOUREA COMPOUNDS AND USE

[75] Inventors: Fatih M. Uckun, White Bear Lake; Taracad K. Ventatachalam, St. Anthony, both of Minn.

[73] Assignee: Hughes Institute, Roseville, Minn.

[21] Appl. No.: 09/338,685

[22] Filed: Jun. 23, 1999

[51] Int. Cl.$^7$ .......................... A61K 31/44; A61K 31/38; C07D 333/34; C07D 333/22; C07D 333/42
[52] U.S. Cl. .......................... 514/336; 514/438; 549/65; 549/77; 549/68; 546/280.4
[58] Field of Search .................. 546/280.4; 514/336, 514/438; 549/68, 65, 77

[56] References Cited

U.S. PATENT DOCUMENTS

| | | | |
|---|---|---|---|
| 5,593,993 | 1/1997 | Morin, Jr. et al. | 514/332 |
| 5,658,907 | 8/1997 | Morin, Jr. et al. | 514/247 |
| 5,686,428 | 11/1997 | Eriksson et al. | 514/50 |
| 5,714,503 | 2/1998 | Morin, Jr. et al. | 514/247 |

FOREIGN PATENT DOCUMENTS

WO 93/03022  2/1993  WIPO.

OTHER PUBLICATIONS

Bell, et. al., Phenethylthiazolethieourea (PETT) Compounds, a New Class of HIV–1 Reverse Transcriptase Inhibitors. 1. Synthesis and Basic Structure–Activity Relationship Studies of PETT Analogs, J. Med. Chem., vol. 38, pp. 4929–4936, 1995.

Davies et. al., Condensed Thiophen Ring Systems. Part XIX. Synthesis of 6,7–Dihydrothieno [3,2–c] pyridines by Intramolecular Cyclistion of 2–(2– or 3–Thienyl)ethyl Isothiocyanate, Journal of Chemical Society, Perkin Translations 1, vol. 2, pp. 138–14, 1976.

Cantrell, et. al., Phenethylthiazolythiourea (PETT) Compounds as a New Class of HIV–1 Reverse Transcriptase Inhibitors. 2. Synthesis and Further Structure–Activity Relationship Studies of PETT Analogs, J. Med. Chem., 39, 4261–4274, 1996.

Gittos et. al., A New Synthesis of Isocyanates, J. C. S. Perkin I, pp. 169–143, 141.

Ahgren, C., et al., 1995, *Antimicrob. Agents Chemotherapy*, 39, 1329–1335 The PETT Series, a New Class of Potent Nonnucleoside Inhibitors of Human Immunodeficiency Virus Type 1 Reverse Transcriptase.

Bell, F. W., et al., 1995, *J. Med. Chem.*, 38, 4929–4936 Penethylthiazolethiourea (PETT) Compounds, a New Class of HIV–1 Reverse Transcriptase Inhibitors. 1. Synthesis and Basic Structure–Activity Relationship Studies of PETT Analogs.

Bosworth, N., et al., 1989, *Nature*, 341: 167–168 Scintillation proximity assay.

Cantrell, A. S., et al., 1996, *J. Med. Chem.*, 39, 4261–4274 Phenethylthiazolylthiourea (PETT) Compounds as a New Class of HIV–1 Reverse Transcriptase Inhibitors. 2. Synthesis and Further Structure–Activity Relationship Studies of PETT Analogs.

Das, K. et al., 1996, *J. Mol. Biol.*, 264, 1085–1100 Crystal Structures of 8–Cl and 9–Cl TIBO Complexed with Wild–type HIV–1 RT and 8–Cl TIBO Complexed with the Tyr181Cys HIV–1 RT Drug–resistant Mutant.

Ding, J., 1995, et al., *Nat. Struct. Biol.*, 2, 407–415 Structure of HIV–1 TR/TIBO R 86183 complex reveals similarity in the binding of diverse nonnucleoside inhibitors.

Erice, A. et al., 1993, *Antimicrob. Ag. Chemother.*, 37, 835 Anti–Human Immunodeficiency Virus Type 1 Activity of an Anti–CD4 Immunoconjugate Containing Pokeweed Antiviral Protein.

Kohlstaedt, L.A. et al., 1992, *Science*, 256, 1783–1790 Crystal Structure at 3.5 Å Resolution of HIV–1 Reverse Transcriptase Complexed with an Inhibitor.

Mao, C. et al., 1998, *Bioorganic & Medicinal Chemistry Letters* 8, pp. 2213–2218 Structure–Based Design of N–[2–(1–Piperidinylethyl)]–N'–[2–(5–Bromopyridyl)]–Thiourea and N–2–(1–Piperazinylethyl)–N'–[2–(5–Bromopyridyl)]–Thiourea as Potent Non–Nucleoside Inhibitors of HIV–1 Reverse Transcriptase.

Pauwels, R. et al., 1990, *Nature*, 343, 470–474 Potent and selective inhibitionofHIV–1 replication in vitro by a novel series of TIBO derivatives.

Ren, J. et al., 1995, *Structure*, 3, 915–926 The structure of HIV–1 reverse transcriptase complexed with 9–chloro–TIBO: lessons for inhibitor design.

Romero, D. L. et al., 1993, *J. Med. Chem.*, 36, 1505–1508 Bis(heteroaryl)piperazine (BHAP) Reverse Transcriptase Inhibitors: Structure–Activity Relationships of Novel Substituted Indole Analogues and the Identification of 1–[(5–Methanesulfonamido–1H–indol–2–yl)–carbonyl]–4–[3–[(1–methylethyl)amino]–pyridinyl]piperazine Monomethanesulfonate (U–90152S), a Second–Generation Clinical Candidate.

Sahlberg, et al., 1998, *Bioorganic & Medicinal Chemistry Letters* 8, pp. 1511–1516 Synthesis and Anti–Hiv Activities of Urea–PETT Analogs Belonging to a New Class of Potent Non–Nucleoside HIV–1 Reverse Transcriptase Inhibitors.

Sudbeck, E. A. et al., 1998, *Antimicrobial Agents and Chemotherapy*, 42(12), 3225–33 Structure–Based Design of Novel Dihydroalkoxybenzyloxopyrimidine Derivatives as Potent Nonnucleoside Inhibitors of the Human Immunodeficiency Virus Reverse Transcriptase.

Uckun, F. M. et al., 1998, *Antimicrobial Agents and Chemotherapy*, 42, 383 TXU (Anti–CD7)–Pokeweed Antiviral Protein as a Potent Inhibitor of Human Immunodeficiency Virus.

Vig, R. et al., 1998, *Bioorganic & Medicinal Chemistry*, 6:1789–1797 Rational Design and Synthesis of Phenethyl–5–bromopyridyl Thiourea Derivatives as Potent Non–nucleoside Inhibitors of HIV Reverse Transcriptase.

Zhang et al., 1996, *Antiviral Chemistry & Chemotherapy*, 7(5):221–229 Synergistic inhibition of HIV–1 reverse transcriptase and HIV–1 replication by combining trovirdine with AZT, ddl and ddC in vitro.

*Primary Examiner*—Zinna Northington Davis
*Assistant Examiner*—Binta Robinson
*Attorney, Agent, or Firm*—Merchant & Gould P.C.

[57] ABSTRACT

Novel thiophene-ethyl-thiourea (TET) compounds as inhibitors of reverse transcriptase and effective agents for the treatment of HIV infection, including mutant, drug-sensitive, drug-resistant, and multi-drug resistant strains of HIV.

16 Claims, No Drawings

THIOPHENE-ETHYL THIOUREA COMPOUNDS AND USE

FIELD OF THE INVENTION

The invention relates to inhibitors of reverse transcriptase effective against HIV, including mutant strains of HIV, and effective in the treatment of multi-drug resistant HIV infection.

BACKGROUND OF THE INVENTION

Agents currently used to treat HIV infection attempt to block replication of the HIV virus by blocking HIV reverse transcriptase or by blocking HIV protease. Three categories of anti-retroviral agents in clinical use are nucleoside analogs (such as AZT), protease inhibitors (such as nelfinavir), and the recently introduced non-nucleoside reverse transcriptase inhibitors (NNI), such as nevirapine.

The recent development of potent combination anti-retroviral regimens has significantly improved prognosis for persons with HIV and AIDS. Combination therapies may be a significant factor in the dramatic decrease in deaths from AIDS (a decrease in death rate as well as absolute number). The most commonly used combinations include two nucleoside analogs with or without a protease inhibitor.

Nevirapine is currently the only NNI compound which has been used in combination with AZT and/or protease inhibitors for the treatment of HIV. A new series of effective drug cocktails will most likely involve other NNIs in combination with nucleoside and protease inhibitors as a triple action treatment to combat the growing problem of drug resistance encountered in single drug treatment strategies.

The high replication rate of the virus unfortunately leads to genetic variants (mutants), especially when selective pressure is introduced in the form of drug treatment. These mutants are resistant to the anti-viral agents previously administered to the patient. Switching agents or using combination therapies may decrease or delay resistance, but because viral replication is not completely suppressed in single drug treatment or even with a two drug combination, drug-resistant viral strains ultimately emerge. Triple drug combinations employing one (or two) nucleoside analogs and two (or one) NNI targeting RT provide a very promising therapy to overcome the drug resistance problem. RT mutant strains resistant to such a triple action drug combination would most likely not be able to function.

Dozens of mutant strains have been characterized as resistant to NNI compounds, including L1001, K103N, V106A, E138K, Y188IC and Y188H. In particular, the Y181C and K103N mutants may be the most difficult to treat, because they are resistant to most of the NNI compounds that have been examined.

Recently, a proposed strategy using a knock-out concentration of NNI demonstrated very promising results. The key idea in this strategy is to administer a high concentration of NNI in the very beginning stages of treatment to reduce the virus to undetectable levels in order to prevent the emergence of drug-resistant strains. The ideal NNI compound for optimal use in this strategy and in a triple action combination must meet three criteria:

1) very low cytotoxicity so it can be applied in high doses;
2) very high potency so it can completely shut down viral replication machinery before the virus has time to develop resistant mutant strains; and
3) robust anti-viral activity against current clinically observed drug resistant mutant strains.

Novel NNI designs able to reduce RT inhibition to sub-nanomolar concentrations with improved robustness against the most commonly observed mutants and preferably able to inhibit the most troublesome mutants are urgently needed. New antiviral drugs will ideally have the following desired characteristics: (1) potent inhibition of RT; (2) minimum cytotoxicity; and (3) improved ability to inhibit known, drug-resistant strains of HIV. Currently, few anti-HIV agents possess all of these desired properties.

Two non-nucleoside inhibitors (NNI) of HIV RT that have been approved by the U.S. Food and Drug Administration for licensing and sale in the United States are nevirapine (dipyridodiazepinone derivative) and delavirdine (bis (heteroaryl)piperazine (BHAP) derivative, BHAP U-90152). Other promising new non-nucleoside inhibitors (NNIs) that have been developed to inhibit HIV RT include dihydroalkoxybenzyloxopyrimidine (DABO) derivatives, 1-[(2-hydroxyethoxy)methyl]-6-(phenylthio)thymine (HEPT) derivatives, tetrahydrobenzondiazepine (TIBO), 2',5'-Bis-O-(tert-butyldimethylsilyl)-3'-spiro-5"-(4"-amino-1",2"-oxathiole-2",2'-dioxide)pyrimidine (TSAO), oxathiin carboxanilide derivatives, quinoxaline derivatives, thiadiazole derivatives, and phenethylthiazolylthiourea (PETT) derivatives.

NNIs have been found to bind to a specific allosteric site of HIV-RT near the polymerase site and interfere with reverse transcription by altering either the conformation or mobility of RT, thereby leading to a noncompetitive inhibition of the enzyme (Kohlstaedt, L. A. et al., *Science*, 1992, 256, 1783–1790).

A number of crystal structures of RT complexed with NNIs have been reported (including α-APA, TIBO, Nevirapine, and HEPT derivatives), and such structural information provides the basis for further derivatization of NNI aimed at maximizing binding affinity to RT. However, the number of available crystal structures of RT NNI complexes is limited.

Given the lack of structural information, alternate design procedures must be relied upon for preparing active inhibitors such as PETT and DABO derivatives. One of the first reported strategies for systematic synthesis of PETT derivatives was the analysis of structure-activity relationships independent of the structural properties of RT and led to the development of some PETT derivatives with significant anti-HIV activity (Bell, F. W. et al., *J Med. Chem.*, 1995, 38, 4929–4936; Cantrell, A. S. et al., *J. Med. Chem.*, 1996, 39, 4261–4274).

A series of selected phenethylthiazolylthiourea (PETT) derivatives targeting the NNI binding site of HIV reverse transcriptase (RT) were synthesized and tested for anti-human immunodeficiency virus (HIV) activity. The structure based design and synthesis of these PETT derivatives were aided by biological assays and their anti-HIV activity. Some of these novel derivatives were more active than AZT or Troviridine and abrogated HIV replication at nanomolar concentrations without any evidence of cytotoxicity. These compounds are useful in the treatment of HIV infection, and have particular efficacy against mutant strains, making them useful in the treatment of multi-drug resistant HIV.

SUMMARY OF THE INVENTION

The invention provides novel thiophene-ethyl-thiourea (TET) compounds as newly identified non-nucleoside inhibitors (NNI) of HIV reverse transcriptase. The novel TET compounds, compositions, and methods of the invention are useful in the treatment of HIV infection, with particular efficacy against multiple strains of HIV, including multi-drug resistant mutant strains.

The TET compounds, compositions, and methods of the invention are useful for inhibiting reverse transcriptase activity and inhibiting replication of multiple strains of HIV, including therapy-naive, drug-resistant, and multi-drug resistant strains. In particular, the TET compounds of the invention are useful for treating retroviral infection in a subject, such as an HIV-1 infection, by administration of the TET compounds of the invention, for example, in a pharmaceutical composition.

The TET compounds of the invention contain a thiophene structure as shown in Formula I. The thiophene may be substituted ($R_n$) or unsubstituted. $R_1$ is a cyclic moiety which may be substituted or unsubstituted. The cyclic moiety can be aromatic and/or heterocyclic. One exemplary TET compound of the invention is WH-443, having the specific structure shown in Formula II.

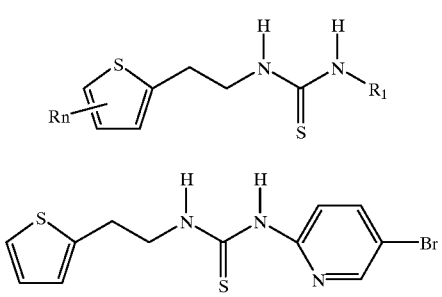

The TET compounds and compositions useful in the invention exhibit very low cytotoxicity and very high potency against HIV.

Specific compounds and methods of the invention are described more fully in the Detailed Description and in the Examples below.

DETAILED DESCRIPTION OF THE INVENTION Definitions

When used herein, the following terms have the indicated meanings:

"NNI" means non-nucleoside inhibitor. In the context of the invention, non-nucleoside inhibitors of HIV reverse transcriptase (RT) are defined.

"Mutant HIV" means a strain of HIV having one or more mutated or altered amino acids as compared with wild type.

"Multi-Drug Resistant HIV" means one or more HIV strain which is resistant to treatment with one or more chemotherapeutic agent.

"Therapeutically effective amount" is a dose which provides some therapeutic benefit on administration, including, in the context of the invention, reduced viral activity or viral load in a patient, and also including inhibition of viral RT activity and/or replication of virus.

Compounds of the Present Invention

Compounds of the present invention are thiophene-ethyl-thiourea (TET) compounds useful as non-nucleoside inhibitors of RT having the formula I:

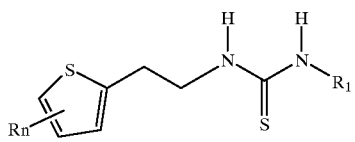

The thiophene may be substituted or unsubstituted, for example, R can be H, halogen, ($C_1$–$C_{12}$) alkyl or alkoxy, amino, cyano, nitro, hydroxy, and the like. The value of n can be 0 to 4. $R_1$ is a cyclic moiety, which may be substituted or not, such as phenyl, pyridyl, piperidinyl, piperonyl, morpholyl, furyl, and the like, and can be, for example, cyclo($C_3$–$C_{12}$) alkyl, cyclo($C_3$–$C_{12}$) alkenyl, isothiazolyl, tetrazoyl, triazolyl, pyridyl, imidazolyl, phenyl, napthyl, benzoxazolyl, benzimidazolyl, thiazolyl, oxazolyl, benzothiazolyl, pyrazinyl, pyridazinyl, thiadiazolyl, benzotriazolyl, pyrolyl, indolyl, benzothienyl, thienyl, benzofuryl, quinolyl, isoquinolyl, pyrazolyl, and the like.

In one preferred embodiment, $R_1$ is pyrididyl, optionally substituted with one or more substituents, for example, with an alkyl, alkoxy, halo, or hydroxy group. More preferably, $R_1$ is pyridyl substituted with a halogen such as bromine or chlorine. An exemplary compound of the invention is N-[2-(2-thiophene)ethyl-N-[2-(5-bromopyridyl)]-thiourea (HI-443), where $R_1$ is pyridyl, substituted with a halogen, bromine.

The compounds of the invention preferably bind to a specific allosteric site of HIV-RT near the polymerase site and interfere with reverse transcription, for example, by altering either the conformation or mobility of RT.

Acid salts

The compounds of the invention may also be in the form of pharmaceutically acceptable acid addition salts. Pharmaceutically acceptable acid addition salts are formed with organic and inorganic acids.

Examples of suitable acids for salt formation are hydrochloric, sulfuric, phosphoric, acetic, citric, oxalic, malonic, salicylic, malic, gluconic, fumaric, succinic, asorbic, maleic, methanesulfonic, and the like. The salts are prepared by contacting the free base form with a sufficient amount of the desired acid to produce either a mono or di, etc. salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention. Use of excess base where R is hydrogen gives the corresponding basic salt.

Methods of Using the Compounds of the Invention

The compounds of the invention are useful in methods for inhibiting reverse transcriptase activity of a retrovirus. Retroviral reverse transcriptase is inhibited by contacting RT in vitro or in vivo, with an effective inhibitory amount of a compound of the invention. The compounds of the invention also inhibit replication of retrovirus, particularly of HIV, such as HIV-1. Viral replication is inhibited, for example, by contacting the virus with an effective inhibitory amount of a compound of the invention.

The methods of the invention are useful for inhibiting reverse transcriptase and/or replication of multiple strains of HIV, including mutant strains, and include treating a retroviral infection in a subject, such as an HIV-1 infection, by administering an effective inhibitory amount of a compound or a pharmaceutically acceptable acid addition salt of a compound of the Formula I. The compound or inhibitor of Formula I is preferably administered in combination with a pharmaceutically acceptable carrier, and may be combined with specific delivery agents, including targeting antibodies and/or cytokines. The compound or inhibitor of the invention may be administered in combination with other antiviral agents, immunomodulators, antibiotics or vaccines.

The compounds of Formula I can be administered orally, parentally (including subcutaneous injection, intravenous, intramuscular, intrastemal or infusion techniques), by inhalation spray, topically, by absorption through a mucous membrane, or rectally, in dosage unit formulations containing conventional non-toxic pharmaceutically acceptable carriers, adjuvants or vehicles. Pharmaceutical compositions of the invention can be in the form of suspensions or tablets suitable for oral administration, nasal sprays, creams, sterile injectable preparations, such as sterile injectable aqueous or oleagenous suspensions or suppositories. In one embodiment, the TET compounds of the invention can be applied intravaginally and/or topically, for example in gel form, for prevention of heterosexual transmission of HIV.

For oral administration as a suspension, the compositions can be prepared according to techniques well-known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents and lubricants known in the art.

For administration by inhalation or aerosol, the compositions can be prepared according to techniques well-known in the art of pharmaceutical formulation. The compositions can be prepared as solutions in saline, using benzyl alcohol or other suitable preservatives, absorption promoters to enhance bioavailability, fluorocarbons or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or diglycerides, and fatty acids, including oleic acid.

For rectal administration as suppositories, the compositions can be prepared by mixing with a suitable non-irritating excipient, such as cocoa butter, synthetic glyceride esters or polyethylene glycols, which are solid at ambient temperatures, but liquefy or dissolve in the rectal cavity to release the drug.

Dosage levels of approximately 0.02 to approximately 10.0 grams of a compound of the invention per day are useful in the treatment or prevention of retroviral infection, such as HIV infection, AIDS or AIDS-related complex (ARC), with oral doses 2 to 5 times higher. For example, HIV infection can be treated by administration of from about 0.1 to about 100 milligrams of compound per kilogram of body weight from one to four times per day. In one embodiment, dosages of about 100 to about 400 milligrams of compound are administered orally every six hours to a subject. The specific dosage level and frequency for any particular subject will be varied and will depend upon a variety of factors, including the activity of the specific compound the metabolic stability and length of action of that compound, the age, body weight, general health, sex, and diet of the subject, mode of administration, rate of excretion, drug combination, and severity of the particular condition.

The compound of Formula I can be administered in combination with other agents useful in the treatment of HIV infection, AIDS or ARC. For example, the compound of the invention can be administered in combination with effective amounts of an antiviral, immunomodulator, anti-infective, or vaccine. The compound of the invention can be administered prior to, during, or after a period of actual or potential exposure to retrovirus, such as HIV.

Conjugation to a Targeting Moiety

The compound of the invention can be targeted for specific delivery to the cells to be treated by conjugation of the compounds to a targeting moiety. Targeting moiety useful for conjugation to the compounds of the invention include antibodies, cytokines, and receptor ligands expressed on the cells to be treated.

The term "conjugate" means a complex formed with two or more compounds.

The phrase "targeting moiety" means a compound which serves to deliver the compound of the invention to a specific site for the desired activity. Targeting moieties include, for example, molecules which specifically bind molecules present on a cell surface. Such targeting moieties useful in the invention include anti-cell surface antigen antibodies. Cytokines, including interleukins, factors such as epidermal growth factor (EGF), and the like, are also specific targeting moieties known to bind cells expressing high levels of their receptors.

Particularly useful targeting moieties for targeting the compounds of the invention to cells for therapeutic activity include those ligands that bind antigens or receptors present on virus-infected cells to be treated. For example, antigens present on T-cells, such as CD48, can be targeted with antibodies. Antibody fragments, including single chain fragments, can also be used. Other such ligand-receptor binding pairs are known in the scientific literature for targeting anti-viral treatments to target cells. Methods for producing conjugates of the compounds of the invention and the targeting moieties are known.

Methods of Making the Compounds of the Invention

The compounds of the invention may be prepared as shown in Schemes 1 and 2. In general, an appropriate amine ($R_1$—$NH_2$) is reacted with 1,1'-thiocarbonyl-diimidazole in acetonitrile solvent at ambient temperature for approximately 12 hours to form a thiocarbonyl reagent. The reaction product is then condensed with a substituted or non-substituted thioethyl amine in an aprotic solvent such as dimethyl-formamide (DMF) at elevated temperature, such a 100° C., for an extended period of time such as about 15 hours. The desired TET compound is purified by column chromatography.

Scheme 1:

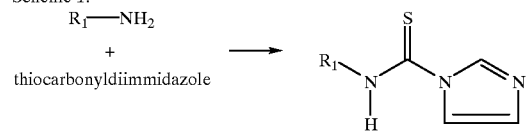

Scheme 2:

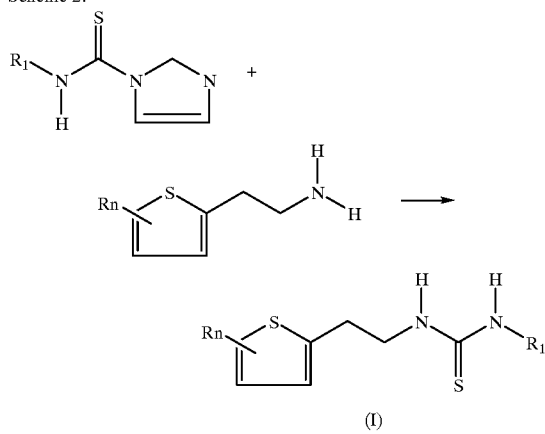

The TET compounds of the invention can be synthesized as described above, or by other know synthetic methods.

EXAMPLES

The invention may be further clarified by reference to the following Examples, which serve to exemplify the embodiments, and not to limit the invention in any way.

Example 1

Comparison of Substituted Thiourea Compounds

Recently, we reported that the replacement of the planar pyridyl ring of trovirdine with a puckered piperidinyl or piperazinyl ring, which occupy larges volumes, would better fill the spacious Wing 2 region of the butterfly-shaped NNI binding pocket (Mao et. l., 1998, *Bioor. Medicinal Chem. Lett.* 8:2213–2218). Such heterocyclic rings are conformationally more flexible than an aromatic ring and hence are likely to have an added advantage by being able to fit an uncompromising binding pocket more effectively, despite the expense paid for loss of entropy upon binding.

The first two heterocyclic compounds synthesized were N-[2-(1-piperidinylethyl)]-N'[2-(5-bromopyridyl)]-thiourea (HI-172) and N-[2-(1-piperazinylethyl)]-N'[2-(5-bromopyridyl)]-thiourea (Mao et. al, surpra). When analized for antiviral acitivity, both heterocyclic compounds were more potent than trovirdine and abrogated the replication of the NNI-sensitive HIV-1 strain $HTLV_{IIIB}$ in human peripheral blood mononuclear cells (PBMC) at nanomolar concentrations. However, unlike trovirdine, neither compound inhibited the replication of NNI-resistant HIV-1 strains (Mao et. al, 1999, *Bioorg. Med. Chem. Lett.* 9:1593–1598). These initial findings demonstrated that the replacement of the pyridyl ring of trovirdine with a bulky ring produces useful compounds, however, the new compound may not retain the ability to inhibit HIV-1 strains having RT mutations.

To further understand the structure-function relationships of RT-NNIs and to discover novel, effective NNIs, we replaced the pyridyl ring of trovirdine with one of eight different heterocyclic substituents, including:

a. the heterocyclic amines pyrrolidine, 1-methylpyrrolidine, morpholine, imidazole, indole;

b. heterocyclic aromatic groups furan and thiophene; and c. the aromatic aldehyde piperonyl.

Synthesis of Compounds:

The thiourea compounds were synthesized as described in schemes 3 and 4.

In brief, 2-amino-5-bromopyridine was condensed with 1,1-thiocarbonyl diimidazole to furnish the precursor thiocarbonyl derivative. Further reaction with appropriately substituted phenylethyl amine gave the target compound in good yields.

Specifically, thiocarbonyldiimidazole (8.90 g, 50 mmol) and 2amino-5-bromo pyridine (8.92 g, 50 mmol) were added to 50 mL of dry acetonitrile at room temperature. The reaction mixture was stirred for 12 hours and the precipitate filtered, washed with cold acetonitrile (2×25 mL), and dried under vacuum to afford (1 1.40 g, 80% ) of compound A. To a suspension of compound A (0.55 eqv) in dimethyl formamide (15mL) an appropriate amine (0.50 eqv) was added. The reaction mixture was heated to 100° C. and stiffed for 15 hours. The reaction mixture was poured into ice-cold water and the suspension was stirred for 30 minutes. The product was filtered, washed with water, dried, and further purified by column chromatography to furnish the target compounds in good yields. Trovidine, a comparative standard, was prepared by the method described in Bell et al., *J Med. Chem* 1995, 38:4926–9; Ahgren et. al., 1995, *Antimicrob. Agents Chemotherapy* 39:1329–1335.

Scheme 3:

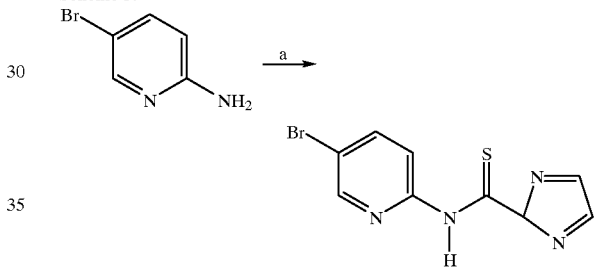

Scheme 4:

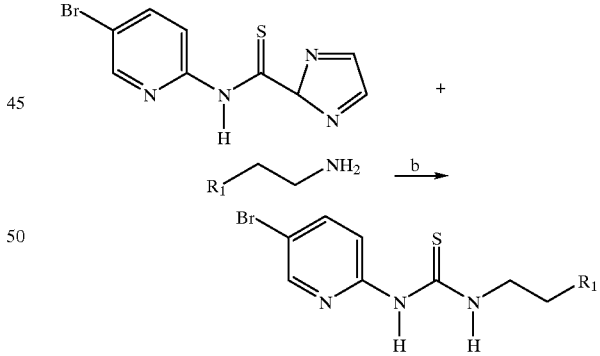

a=1,1'-thiocarbonyl diimidazole, acetonitrile, room temperature, 12 hours b=DMF, 100° C., 15 hours $R_1$ is shown in Table 1

Characterization of synthesized compounds:

Proton and carbon nuclear magnetic resonance spectra were recorded on a Varian spectrometer using an automatic broad band probe. Unless otherwise noted, all NMR spectra were recorded in $CDCl_3$ at room temperature. The chemical shifts reported are in parts per million relative to tetramethyl silane as standard. The multiplicity of the signals were designated as follows: s, d, dd, t, q, m which corresponds to singlet, doublet, doublet of doublet, triplet, quartet and multiplet respectively. UV spectra were recorded from a Beckmann Model # DU 7400 UV/Vis spectrometer using a cell path length of 1cm. Fourier Transform Infra Red spectra were recorded using an FT-Nicolet model Protege #460 instrument. The infra red spectra of the liquid samples were run as neat liquids using KBr discs. Mass spectrum analysis was conducted using either a Finnigan MAT 95 instrument or a Hewlett-Packard Matrix Assisted Laser Desorption (MALDI) spectrometer model # G2025A. The matrix used in the latter case was cyano hydoxy cinnamic acid. Melting points were determined using a Melt John's apparatus and uncorrected. Elemental analysis were was performed by Atlantic Microlabs (Norcross, Ga.). Column chromatography was performed using silica gel obtained from the Baker Company. The solvents used for elution varied depending on the compound and included one of the following: ethyl acetate, methanol, chloroform, hexane, methylene chloride and ether. Characterizataion data for the synthesized compounds is shown below:

N-[2-(2-fluorophenethyl)]-N'-[2-(5-bromopyridyl)]thiourea (HI-240):

Yield: 71%, mp 156–157° C.; UV (MeOH) λmax: 209, 256, 274, 305 nm; IR(KBr) ν 3446, 3234, 3163, 3055, 2935, 1672, 1595, 1560, 1531, 1466, 1390, 1362, 1311, 1265, 1227, 1169, 1136, 1089, 1003, 864, 825, 756 cm$^{-1}$; $^1$HNMR (CDCl$_3$) δ 11.36 (bs, 1H), 9.47 (bs, 1H), 8.05–8.04 (dd, 2H), 7.29–7.24 (m, 1H), 7.13–7.03 (m, 3H), 6.87–6.84 (d, 1H), 4.06–3.99 (q, 2H), 3.10–3.05 (t, 2H), $^{13}$C(CDCl$_3$) δ 179.1, 151.7, 146.2, 141.1, 131.2, 131.1, 128.5, 128.4, 124.1, 115.5, 115.2, 113.6, 112.2, 45.8 and 28.2; $^{19}$F(CDCl$_3$) δ–42.58 &–42.55 (d); Maldi Tof mass: 355 (M+1), Calculated mass: 354; Anal. (C$_{14}$H$_{13}$BrFN$_3$S) C, H, N, S;

N-[2-(1-pyrolidylethyl)]-N'-[2-(5-bromopyridyl)]thiourea (HI-230):

Yield: 72%; mp. 136–138° C.; UV (MeOH) λmax: 203, 206, 252, 277, 306 nm IR(KBr)ν 3454, 3220, 3159, 3059, 2941, 2787, 1595, 1531, 1475, 1311, 1229, 1182, 1067, 1003, 864, 821, 706 cm$^{-1}$; $^1$HNMR (CDCl$_3$) δ 11.53 (bs, 1H), 9.17 (bs, 1H), 8.19–8.11 (d, 1H), 7.73–7.69 (d, 1H), 6.82–6.79 (dd, 1H), 3.85–3.83 (q, 2H), 2.79(t, 2H), 2.60 (bm, 4H), 1.81 (bm); $^{13}$C(CDCl$_3$) δ 178.7, 151.7, 146.5, 141.1, 113.4, 112.7, 53.8, 53.6, 44.9 and 23.7; Maldi Tof mass: 329 (M+1), Calculated mass: 328; Anal. (C$_{12}$H$_{17}$BrN$_4$S), Found: C: 42.64, H: 4.80, N:16.71, S: 7.72, Br: 28.04;

N-[2-(1-piperonyl)]-N'-[2-(5-bromopyridyl)]thiourea (HI-257):

Yield: 70%; mp 159–162° C.; UV (MeOH) λmax: 209, 276 nm, IR(KBr) ν 3450, 3215, 3151, 3082, 3009, 2931, 1591, 1562, 1529, 1500, 1475, 1305, 1238, 1168, 1086, 1041, 933, 858, 825, 794, 688 cm$^{-1}$; $^1$HNMR (DMSO-d$_6$) δ 11.64 (bs, 1H), 10.68 (bs, 1H), 8.17–8.16(s, 1H), 7.75–7.72 (d, 1H), 7.19–7.16 (d, 1H), 6.91–6.90 (s, 1H), 6.84–6.83 (d, 1H), 6.79–6.77(d, 1H), 6.01 (s, 2H), 4.86–4.84 (d, 2H); $^{13}$C(CDCl$_3$) δ 178.7, 151.3, 146.4, 144.7, 139.7, 130.3, 119.5, 113.5, 10.9, 106.9, 99.7 and 47.3, Maldi Tofmass: 366 (M+Na), Calculated mass: 345; Anal. (C$_{14}$H$_{12}$Br N$_3$O$_2$S) C, H, N, S, Br;

N-[2-(1-piperidinoethyl)]-N'-[2-(5-bromopyridyl)]thiourea (HI-172):

Yield: 74%; m.p. 150–152° C.; R$_f$=0.74 in CHCl$_3$:MeOH (9:1); UV (MeOH) λmax: 306, 275 and 205 nm, IR(KBr)ν 3155, 3077, 2935, 2850, 2360, 1591, 1525, 1465, 1319, 1226, 1095, 827 and 756 cm$^{-1}$; $^1$HNMR (CDCl$_3$) δ 11.53 (s, 1H), 9.72 (s, 1H), 8.22 (s, 1H), 7.72–7.68 (d, 1H), 6.95–6.92 (d, 1H), 3.84–3.78 (q, 2H), 2.61–2.57 (t, 2H), 2.45 (bs, 4H), 1.64–1.48 (m, 6H); $^{13}$C(CDCl$_3$) δ 178.1, 151.8, 146.3, 140.8, 113.5, 112.6, 56.1, 54.0, 43.0, 26.3 and 24.3; Mass observed on MALDI-TOF: 343.5; Exact Mass=343. Anal. (C$_{13}$H$_{19}$BrN$_4$S) C, H, N, S, Br;

N-[2-(1-methyl-2-pyrrolidinylethyl)]-N'-[2-(5 bromopyridyl)]thiourea (HI-206):

Yield: 56%; R$_f$=0.34 in CHCl$_3$:MeOH (9:1); UV (MeOH) λmax 307, 276, 256 and 207 nm, IR(KBr)ν 3207, 2944, 2782, 2360, 1591, 1467, 1307, 1226, 1093 and 825 cm$^{-1}$; $^1$HNMR (CDCl$_3$) δ 11.18 (s, 11H), 8.80 (s, 1H), 8.22 (s, 11H), 7.74–7.70 (d, 1H), 6.75–6.72 (d, 1H), 3.82–3.72 (q, 2H), 3.61–3.54 (m, 1H), 3.14–3.04 (t, 2H), 2.34 (s, 3H), 2.19–1.60 (m, 6H); $^{13}$C(CDCl$_3$) δ 178.9, 146.9, 140.8, 113.3, 112.2, 64.2, 57.2, 43.4, 40.7, 32.4, 30.5 and 22.2; Mass observed on MALDI-TOF : 343.6; Exact Mass 343; Anal. (C$_{13}$H$_{19}$BrN$_4$S) Found: C: 45.49, H: 5.58, N:16.32 S: 9.34, Br: 23.28;

N-[2-(5-Bromopyridinyl)]-N'-[2-(2-Imidazolylethyl)]thiourea (HI-436):

Yield 44%; mp: 104–107° C.; UV(MeOH) λ$_{max}$: 208, 275, 305 nm; IR(KBr)ν 3490, 3228, 3097, 2944, 2618, 1592, 1529, 1502, 1463, 1301, 1267, 1228, 1199, 1095, 937, 862, 827, 784, 750, 661, 595 cm$^{-1}$; $^1$HNMR(DMSO) δ 11.12 (bs, 1H), 10.13 (bs, 1H), 7.82–7.81 (d, 1H), 7.41–7.38 (dd, 1H), 7.33 (s, 1H), 6.80–6.77 (d, 1H), 6.61 (s, 1H), 4.89 (bs, 1H), 3.76–3.69 (q, 2H), 2.73–2.68 (t, 2H); $^{13}$C NMR (DMSO) δ 178.3, 151.4, 144.8, 25 139.8, 134.0, 133.9, 116.2, 113.4, 111.1, 44.2, 25.4; MALDI-TOF found: 327.6;

N-[2-(5-Bromopyridinyl)]-N'-[2-(2-Thiophenylethyl)]thiourea (HI-443):

Yield 40%; mp: 160–161° C.; UV(MeOH) λ$_{max}$: 260, 276, 306 nm; IR(KBr) ν 3218, 3151, 3087, 2935, 2873, 1594, 1552, 1531, 1332, 1297, 1265, 1224, 1188, 1134, 1089, 1076, 1006, 833, 811, 784, 742, 688, 582, 503 cm$^{-1}$; $^1$H NMR (CDCl$_3$) δ 11.45 (bs, 1H), 10.40 (bs, 1H), 8.03 (s, 1H), 7.68–7.64 (dd, 1H), 7.20–7.19 (d, 1H), 7.08–7.04 (dd, 111), 6.99–6.95(m, 1H), 6.91 (s, 1H), 4.04–3.97 (q, 2H), 3.24–3.20 (t, 2H); $^{13}$C NMR (CDCl$_3$) δ 179.1, 151.7, 145.1, 140.6, 140.1, 126.2, 124.8, 123.3, 113.8, 111.5, 46.1, 28.4;

N-[2-(5-Bromopyridinyl)]-N'-[2-(3-Indolylethyl)]thiourea (HI-442):

Yield 44%; mp: 208–209° C.; UV(MeOH) λ$_{max}$: 222, 274, 305 nm; IR(KBr) ν 3351, 3207, 3147, 3079, 3035, 2915, 2869, 2840, 1591, 1556, 1531, 1465, 1421, 1328, 1299, 11230, 1189, 1105, 1004, 950, 906, 860, 831, 752, 644, 588, 509 cm$^1$; $^1$H NMR(CDCl$_3$) δ 11.30 (bs, 11H), 10.32 (bs, 1H), 10.20 (bs, 1H), 7.81 (d, 1H), 7.65–7.58 (m, 2H), 7.41–7.39 (d, 1H), 7.16–7.11 (t, 2H), 7.05–7.00 (t, 2H), 4.06–4.00 (q, 2H), 3.15–3.11 (t, 2H); $^{13}$C NMR(CDCl$_3$)δ 178.4, 151.6, 144.9, 139.8, 135.7, 126.4, 122.0, 120.6, 117.9, 117.7, 113.5, 111.1, 111.0, 110.7, 45.4, 23.7;

N-[2-(5-Chloropyridinyl)]-N'-[2-(2-Imidazolylethyl)]thiourea (HI-446):

Yield 56%; mp: 175° C.; UV(MeOH) λ$_{max}$:209, 274, 307 nm; IR(KBr) ν 3494, 3226, 3089, 2944, 2620, 1598, 1556, 1531, 1465, 1390, 1311, 1267, 1230, 1197, 1110, 1008, 937, 864, 827, 784, 752, 663, 621, 597, 507, 474 cm$^{-1}$; $^1$H NMR (CDCl$_3$) δ 11.38 (bs, 1H), 10.40 (bs, 1H), 7.99–7.98 (t, 1H), 7.72–7.68 (dd, 1H), 7.7.56–7.52 (dd, 2H),7.13–7.10 (d, 11H), 6.86 (s, 11H), 4.02–3.96 (q, 2H), 2.98–2.94 (t, 2H); $^{13}$C NMR (CDCl$_3$) δ 178.4, 151.2, 142.5, 137.2, 133.9, 123.2, 112.9, 44.2, 25.5;

N-[2-(5-Bromopyridinyl)]-N'-[2-(2-Furylmethyl)]thiourea (HI-503):

Yield 44%; mp: 187–188° C.; UV(MeOH)λ$_{max}$: 209, 276, 307 4nm; IR(KBr) ν 3216, 3155, 3083, 3037, 2921, 1594, 1550, 1529, 1463, 1307, 1228, 1176, 1135, 1093, 1006, 968, 864, 817, 719, 568 cm$^{-1}$;$^1$H NMR (DMSO) δ 11.50 (t, 5H), 10.86 (bs, 1H), 8.32–8.31 (d, 1H), 7.99–7.95 (dd, 1H), 7.60 (t, 1H), 7.17–7.14 (d, 1), 6.42–6.35(m, 2H), 4.87–4.85 (d, 2H); $^{13}$C NMR (DMSO)δ 179.8, 152.5, 151.0, 146.3, 142.7, 141.7, 114.8, 112.3, 110.8, 107.8, 41.6;

N-[2-(5-Bromopyridinyl)]-N'-[2-(4-Morpholinoethyl)]thiourea (HI-276):

Yield 43%; mp: 159–1608° C.; UV(MeOH)$\lambda_{max}$: 207, 275, 306 nm; IR(KBr) v 3209, 3153, 3079, 3025, 2942, 2852, 2807, 1592, 1562, 1533, 1465, 1334, 1299, 1228, 1199, 1143, 1112, 1018, 943, 912, 862, 831, 727, 700, 507 cm$^{-1}$; $^1$H NMR (CDCl$_3$) δ 11.52 (bs, 1H), 9.24 (bs, 1H, 8.25 (s, 1H), 7.76–7.72 (dd, 1H ), 6.89–6.82 (t, 1H), 3.87–3.75 (m, 64.), 2.69–2.55 (m, 6H ); $^{13}$C NMR(CDCl$_3$)δ 178.6, 151.7, 146.5, 141.1, 113.5, 112.8, 67.2, 55.9, 53.1, 042.5;

N-[2-(5-Bromopyridinyl)]-N'-[2-(Pyridinyl)]thiourea (HI-142):

Yield 54%; mp: 152–154° C.; UV(MeOH) $\lambda_{max}$: 208, 273, 306, 485 m; IR(KBr) v 3224, 3156, 3085, 3039, 2931, 1583, 1558, 1531, 1465, 1432, 1361, 1319, 1263, 1228, 1166, 1135, 1095, 1012, 885, 825, 756, 700, 661, 567, 511cm$^-$; $^1$H NMR(CDCl$_3$)δ 11.55(bs, 1H), 9.56 (bs, 1H), 8.61–8.60 (d, 11), 8.08–8.07 (d, 1H), 7.71–7.62 (m, 2H ), 7.29–7.18 (m, 214), 6.89–7.86 (d, 1H), 4.24–4.17 (q, 2H), 3.25–3.21 (t, 2H); $^{13}$C NMR (CDCl$_3$) δ 178.7, 158.6, 151.6, 148.9, 146.2, 140.9, 136.6, 123.6, 121.6, 113.5, 112.6, 44.9, 36.6;

N-[2-(2-pyridylethyl)]-N'-[2-(pyridyl)]thiourea (111–207):

Yield: 49%, R$_f$70.68 in CHCl$_3$:MeOH (9:1); UV (MeOH) $\lambda_{max}$ 293, 265 , 247 and 209 nm, IR(KBr) v 3415, 3222, 3050, 2360, 1600, 1533, 1479, 1436, 1315, 1240, 1151 and 775 cm$^{-1}$; $^1$HNMR (CDCl$_3$) δ 11.90 (s, 1H), 8.8 (s, 1H), 8.60–8.58 (d, 2H), 8.03–8.01 (d, 1H), 7.65–7.56 (m, 2H), 7.27–7.14 (m, 2H), 6.93–6.89 (d, 1H), 6.80–6.77 (d, 1H) 4.23–4.15 (q, 2H) and 3.41–3.20 (t, 2H); $^{13}$C(CDCl$_3$) δ 179.2, 158.9, 153.0, 149.2, 145.5, 138.5, 136.4, 123.5, 121.4, 117.7, 111.8, 44.9 and 36.9; Mass observed on MALDI-TOF :257.1; Exact Mass=258. Anal. (C$_{13}$H$_{14}$N$_4$S) C, H, N, S;

N-[2-(1-piperizinylethyl)]-N'-[2-(5-bromopyridyl)]thiourea (HI-258):

Yield: 75%,; mp. 178–180° C.; UV (MeOH) λmax 209, 275, 305, IR(KBr)v 3448, 3223, 3159, 3034, 2812, 1666, 1595, 1466, 1435, 1308, 1229, 1130, 1092, 1000, 833 cm$^-$; $^1$HNMR (CDCl$_3$) δ $^1$ HNMR (CDCl$_3$) δ 11.50 (s, 1H), 9.77 (s, 1H), 8.19–8.11 (d, 2H), 7.75–7.71 (d, 2H), 6.97–6.95 (d, 2H), 3.87–3.86 (q, 2H), 3.63–3.60 (t, 2H), 3.45–3.42(t, 2H), 2.74–2.69 (t, 2H), 2.59–2.52(m, 4H); C(CDCl$_3$) δ 178.7, 160.8, 151.8, 146.1, 141.0, 113.7, 112.7, 55.2, 52.1, 51.9, 45.8, 42.5 and 40.1; Mass observed on MALDI-TOF: 343.5; Exact Mass=343; Anal. (C$_{12}$H$_{18}$BrN$_5$S) Found: C: 41.98, H: 4.88, N: 18.74 S: 8.52 Br: 21.58.

Purified RT Assays for Anti-HIV Activity

The synthesized compounds were tested for RT inhibitory activity (IC$_{50}$[rRT]) against purified recombinant HIV RT using the cell-free Quan-T-RT system (Amersham, Arlington Heights, Ill.), which utilizes the scintillation proximity assay principle as decribed in Bosworth, et al., 1989, *Nature* 341:167–168. In the assay, a DNA/RNA template is bound to SPA beads via a biotin/strepavidin linkage. The primer DNA is a 16-mer oligo(T) which has been annealed to a poly(A) template. The primer/template is bound to a strepavidin-coated SPA bead.

$^3$H-TTP is incorporated into the primer by reverse transcription. In brief, $^3$H-TTP, at a final concentration of 0.5 μCi/sample, was diluted in RT assay buffer (49.5 mM Tris-Cl, pH 8.0, 80 mM KCl, 10 Mm MgCl$_2$, 10 mM DTT, 2.5 mM EGTA, 0.05% Nonidet-P-40), and added to annealed DNA/RNA bound to SPA beads. The compound being tested was added to the reaction mixture at 0.001 μM-100 μM concentrations. Addition of 10 mU of recombinant HIV RT and incubation at 37° C. for 1 hour resulted in the extension of the primer by incorporation of $^3$H-TTP. The reaction was stopped by addition of 0.2 ml of 120 mM EDTA. The samples were counted in an open window using a Beckman LS 7600 instrument and IC$_{50}$ values were calculated by comparing the measurements to untreated samples. Data are shown below in Table 1.

TABLE 1

HIV-RT inhibitory activity of HI-443

| Compound | R$_1$ | IC$_{50}$ rRT (μM) | IC$_{90}$ rRT μM |
|---|---|---|---|
| Trovirdine | (Pyridine) | 0.6 | 12 |
| HI-443 | (Thiophene) | 0.8 | 15 |
| HI-230 | (Pyrrolidine) | 4.9 | >100 |
| HI-436 | (Imidazole) | >100 | >100 |
| HI-442 | (Indole) | 0.9 | >100 |
| HI-206 | (1-Methylpyrrolidine) | >100 | >100 |
| HI-276 | (Morpholine) | >100 | >100 |

TABLE 1-continued

HIV-RT inhibitory activity of HI-443

| Compound | R₁ | IC$_{50}$ rRT ($\mu$M) | IC$_{90}$ rRT ($\mu$M) |
|---|---|---|---|
| HI-257 | (Piperonyl) | 0.7 | >100 |
| HI-503 | (Furan) | 1.2 | >100 |

As shown in Table 1, substitution of its pyridyl ring had a major impact on the RT-inhibitory function of trovirdine. Except for trovirdine, only the thiophene-ethyl thiurea (TET) compound N'-[2-(2-thiophene)ethyl]-N'-[2-(5-bromopyridyl)]-thiourea (HI-443) inhibited recombinant RT in vitro by more than 90%. HI-443 inhibited recombinant RT with an IC$_{50}$ value of 0.8 $\mu$M and an IC$_{90}$ value of 12 $\mu$M.

The thiophene group of HI-443 occupies the same Wing 2 region of the NNI binding pocket of RT as trovirdine, but it has a smaller molecular volume. Furthermore, the predicted docked position of HI-443 in the RT binding site hinders an optimum hydrogen bond donor geometry. Therefore, it was not surprising that HI-443 had a slightly lower inhibitory activity on recombinant RT than trovirdine (IC$_{50}$ =0.8 $\mu$M) or our previously published lead compound, HI-172, which has a bulky heterocyclic substituent piperidinyl (IC$_{50}$ =0.6 $\mu$M) (Mao et. al., 1998, *Bioorg. Med. Chem. Lett.* 8:2213) (See Table 1).

Example 3

Comparison of TET Compounds with Other NNI

The anti-HIV activity of the TET compound, HI-443 was compared with that of trovirdine, as well as with the heterocyclic NNI, HI-172 (Mao et. al., 1998, *Bioorg. Med. Chem. Lett.* 8:2213), using the purified recombinant RT and Quan-T-RT assay system as described above for Example 2.

In addition, the anti-HIV activity of the compounds was measured by determining their ability to inhibit the replication of the HIV-1 strains HTLVIIIB, RT-MDR, A17, and A17 variant in peripheral blood mononuclear cells (PBMC) from healthy volunteer donors, using the method described in Uckun et.al., 1998, *Antimicrobial Agents and Chemotherapy* 42:383.

Normal human peripheral blood mononuclear cells (PBMNC) from HIV-negative donors were cultured 72 hours in RPMI 1640 supplemented with 20% (v/v) heat-inactivated fetal bovine serum (FBS), 3% interleukin-2,2 mM L-glutairine, 25 mM HEPES, 2 $\mu$L, NAHCO, 50 mg/mL gentamicin, and 4 Ag/mL phytohemagglutinin prior to exposure to HIV-1 or other HIV strain. The cells were then infected with virus at a multiplicity of infection (MOI) of 0.1 during a one-hour adsorption period at 37° C. in a humidified 5% CO2 atmosphere. Subsequently, cells were cultured in 96-well microplates (100 $\mu$L/well; 2×10$^6$ cells/mL, triplicate wells) in the presence of various inhibitor concentrations. Aliquots of culture supernatants were removed from the wells on the 7th day after infection for p24 antigen p24 enzyme immunoassays (EIA), as previously described in Erice et al., 1993, *Antimicrob. Ag. Chemotherapy* 37:385–838. The applied p24 EIA was the unmodified kinetic assay commercially available from Coulter Corporation/Immunotech, Inc. (Westbrook, Me.).

Percent inhibition of viral replication was calculated by comparing the p24 values from the test substance-treated infected cells with p24 values from untreated infected cells (i.e, virus controls).

A Microculture Tetrazolium Assay (MTA), using 2,3-bis(2-methoxy-4-nitro-5-sulfophenyl)-5-[(phenylamino)-carbonyl]-2H-tetrazolium hydroxide (XTT), was performed to evaluate the cytotoxicity of the compounds, using the methods described, for example, in Uckun et.al., 1998, *Antimicrobial Agents and Chemotherapy* 42:383; and Mao et.al., 1998, *Bioorg. Med. Chem. Lett.* 8:2213.

Activity Against Drug-Resistant HIV Strains

The activity of the TET compound, HI-443, was tested against drug sensitive strains (HTLV VIIB), NNI-resistant strains (A17 and Al 7 Variant), as well as multidrug resistant HIV-1 strains (RT-MDR), using the method described in Uckun et. al., 1998, *Antimicrobial Agents and Chemotherapy* 42:383. RT-MDR was obtained through the AIDS Research and Reference Reagent Program, from Dr. Bendan Larder, and is described in Larder et al., 1993, *Nature*, 365, 451–453.

Data are presented in Table 2 as the IC$_{50}$ values for inhibition of HIV p24 antigen production in PBMC (concentration at which the compound inhibits p24 production by 50%). Surprisingly, the TET compound, HI-443, was 10-times more effective against the multidrug resistant HIV-1 strain RT-MDR with a V106A mutation as well as additional mutations involving the RT residues 74V, 41L, and 215Y than against HTLVIIIB.

TABLE 2

ANTI-HIV ACTIVITY

| Compound | $IC_{50}$ rRT ($\mu$M) | $IC_{50}$ HTLV IIIB ($\mu$M) | $IC_{50}$ RT-MDR (V106A) ($\mu$M) | $IC_{50}$ A17 (Y181C) ($\mu$M) | $IC_{50}$ A17 Varient (Y181C, K103N) ($\mu$M) | $CC_{50}$ MTA ($\mu$M) |
|---|---|---|---|---|---|---|
| HI-443     | 5.3  | 0.030  | 0.004 | 0.048 | 3.263 | >100 |
| Trovirdine | 0.8  | 0.007  | 0.020 | 0.500 | >100  | >100 |
| Nevirapine | 23   | 0.034  | 5.000 | >100  | >100  | 10.5 |
| Delavirdine| 1.5  | 0.009  | 0.400 | 50.0  | >100  | 3.6  |
| MKC-442    | 0.8  | 0.004  | 0.300 | N.D   | N.D   | >100 |
| AZT        | >100 | 0.004  | 0.200 | 0.006 | 0.004 | >100 |
| HI-172     | 0.6  | <0.001 | >100  | >100  | >100  | >100 |
| HI-240     | 0.6  | <0.001 | 0.005 | 0.200 | 41    | >100 |

As shown in Table 2, the TET compound, HI-443, effectively inhibited the replication of the HIV-1 strain $HTL_{VIIIB}$ in human peripheral blood mononuclear cells (PBMC) in three of three independent experiments, with an average $IC_{50}$ value of 0.03 FM. In accordance with the higher $IC_{50}$ value of HI-443 against recombinant RT, the $IC_{50}$ value of HI-443 for inhibition of $HTLV_{IIIB}$ replication was 5 times higher than the $IC_{50}$ value of trovirdine and 30-times higher than the $IC_{50}$ value of HI-172.

Surprisingly, HI-443 was ten times more effective against the multi-drug resistant HIV-1 strain RT-MDR, which has a V 106A mutation as well as additional mutations involving the RT residues 74V, 41L, and 215Y, than it was against HTLV IIIB.

HI-443 was almost as potent against the NNI-resistant HIV-1 strain A17 with a Y181C mutation as it was against $HTLV_{IIIB}$ ($IC_{50}$: 0.048 $\mu$M vs 0.030 $\mu$M), and it was capable of inhibiting the trovirdine-resistant A17 variant with Y181C plus K103N mutations in RT ($IC_{50}$: 3.263 $\mu$M), albeit with a 100-fold lower potency than $HTLV_{IIIB}$ (Table 2). HI-443 was 5-times more potent than trovirdine, 1250-times more potent than nevirapine, 100-times more potent than delavirdine, 75-times more potent than MKC-442, 25,000-times more potent than HI-172, 1.25-times more potent than HI-240 (a recently reported fluorine-substituted PETT derivative with potent anti-HIV activity) (Vig et. al., 1998, Bioor. Med. Chem. 6:1789), and 50-times more potent than AZT against the multidrug resistant HIV-1 strain RT-MDR. Similarly, HI-443 was 10-times more potent than trovirdine, 2083-times more potent than nevirapine, 1042-times more potent than delavirdine, 2083-times more potent than HI-172, and 4.2-times more potent than HI-240 against the NNI-resistant HIV-1 strain A17. Finally, HI-443 inhibited the replication of the NNI-resistant HIV-1 strain A17 variant with an $IC_{50}$ value of 3.263 SM, whereas the $IC_{50}$ values of trovirdine, nevirapine, delavirdine, and HI-172 were all >100 $\mu$M and the $IC_{50}$ value of HI-240 was 41 $\mu$M (Table 2). These findings establish the TET compound HI-443 as a novel NNI with potent antiviral activity against NNI-resistant as well as multidrug resistant stains of HIV-1.

All publications, patents, and patent documents described herein are incorporated by reference as if fully set forth. The invention described herein may be modified to include alternative embodiments. All such obvious alternatives are within the spirit and scope of the invention, as claimed below.

What is claimed is:

1. A compound of the formula:

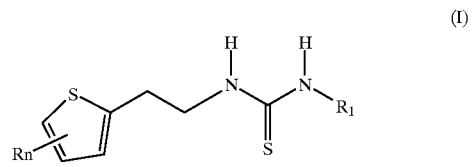

(I)

wherein
n is 0 to 3;
R is H, halogen, ($C_1$–$C_{12}$) alkyl, ($C_1$–$C_{12}$) alkoxy, amino, cyano, nitro, or hydroxy; and
$R_1$ comprises cyclo($C_3$–$C_{12}$) alkyl, cyclo($C_3$–$C_{12}$) alkenyl, isothiazolyl, tetrazolyl, triazolyl, pyridyl, imidazolyl, napthyl, benzoxazolyl, benzimidazolyl, oxazolyl, benzothiazolyl, pyrazinyl, pyridazinyl, thiadiazolyl, benzotriazolyl, pyrolyl, indolyl, benzothienyl, thienyl, benzofuryl, quinolyl, isoquinolyl, or pyrazolyl optionally substituted with one or more substituents selected from the group consisting of ($C_1$–$C_3$) alkyl ($C_1$–$C_3$) alkoxy, halo, or hydroxy; or
a pharmaceutically acceptable addition salt thereof.

2. A compound of the formula:

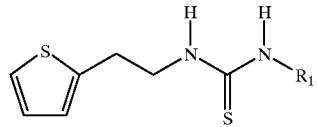

$R_1$ is unsubstituted or substituted pyridyl.

3. The compound of claim 2, having the structure of [2-(2-thiophene)ethyl-N-[2-(5-chloropyridyl)]-thiourea (HI-443); or a pharmaceutically acceptable addition salt thereof.

4. The compound of claim 2, wherein $R_1$ is pyridyl substituted with halogen.

5. The compound of claim 2, wherein $R_1$ is pyridyl substituted with bromine or chlorine.

6. The compound of claim 2, having the structure of [2-(2-thiophene)ethyl-N-[2-(5-bromopyridyl)]-thiourea (HI-443); or a pharmaceutically acceptable addition salt thereof.

7. A pharmaceutical composition comprising a therapeutically effective amount of the compound of claim 4 and a pharmaceutically acceptable carrier or diluent.

8. A method for inhibiting HIV reverse transcriptase comprising contacting said HIV an effective inhibitory amount of a compound of claim 4.

9. A method for treating HIV infection in a subject comprising administering to said subject an anti-HIV effective amount of a compound of claim 4.

10. A method for treating therapy—naïve or drug—resistant HIV in a subject comprising administering to said subject an effective amount of at least one compound of the formula

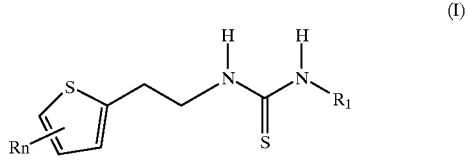

(I)

wherein
  n is 0 to 3;
  R is H, halogen, $(C^1-C_{12})$ alkyl, $(C_1-C_{12})$ alkoxy, amino, cyano, nitro, or hydroxy; and
  $R_1$ comprises cyclo$(C_3-C_{12})$ alkyl, cyclo$(C_3-C_{12})$ alkenyl, isothiazolyl, tetrazolyl, triazolyl, pyridyl, imidazolyl, phenyl, napthyl, benzoxazolyl, benzimidazolyl, thiazolyl, oxazolyl, benzothiazolyl, pyrazinyl, pyridazinyl, thiadiazolyl, benzotriazolyl, pyrolyl, indolyl, benzothienyl, thienyl, benzofuryl, quinolyl, isoquinolyl, or pyrazolyl; or a pharmaceutically acceptable addition salt thereof.

11. A method for treating HIV infection in a subject comprising administering to said subject an anti-HIV effective amount of a compound of claim 2.

12. A method for treating HIV infection in a subject comprising administering to said subject an anti-HIV effective amount of a compound of claim 3.

13. A method for treating therapy—naïve or drug—resistant HIV in a subject comprising administering to said subject an effective amount of at least one compound of claim 6.

14. A method for treating therapy—naïve or drug—resistant HIV in a subject comprising administering to said subject an effective amount of at least one compound of claim 2.

15. A method for treating therapy—naïve or drug—resistant HIV in a subject comprising administering to said subject an effective amount of at least one compound of claim 3.

16. A method for treating HIV infection in a subject comprising administering to said subject an anti-HIV effective amount of a compound of claim 6.

* * * * *